US010112188B2

(12) United States Patent
Frauenrath et al.

(10) Patent No.: US 10,112,188 B2
(45) Date of Patent: Oct. 30, 2018

(54) PROCESS FOR MANUFACTURE OF A ZEOLITE BASED CATALYST FOR THE CONVERSION OF METHANOL TO OLEFINS

(75) Inventors: Manfred Frauenrath, Grosskarolinenfeld (DE); Stefan Klingelhofer, Rosenheim (DE); Gotz Burgfels, Bad Abiling (DE); Avelino Corma Canos, Valencia (ES); Joaquin Martinez Triguero, Manises (ES); Elena Corresa Mateu, Petres (ES)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 789 days.

(21) Appl. No.: 14/005,306

(22) PCT Filed: Mar. 15, 2012

(86) PCT No.: PCT/EP2012/054614
§ 371 (c)(1),
(2), (4) Date: Nov. 13, 2013

(87) PCT Pub. No.: WO2012/123558
PCT Pub. Date: Sep. 20, 2012

(65) Prior Publication Data
US 2014/0079627 A1 Mar. 20, 2014

(30) Foreign Application Priority Data

Mar. 15, 2011 (DE) .................. 10 2011 013 909

(51) Int. Cl.
B01J 29/06 (2006.01)
B01J 29/85 (2006.01)
B01J 29/40 (2006.01)
B01J 37/28 (2006.01)
C07C 1/20 (2006.01)
B01J 37/00 (2006.01)
B01J 29/82 (2006.01)
B01J 37/02 (2006.01)

(52) U.S. Cl.
CPC .............. *B01J 29/85* (2013.01); *B01J 29/40* (2013.01); *B01J 29/82* (2013.01); *B01J 37/0018* (2013.01); *B01J 37/0063* (2013.01); *B01J 37/28* (2013.01); *C07C 1/20* (2013.01); B01J 37/0009 (2013.01); B01J 37/0209 (2013.01); B01J 2229/186 (2013.01); B01J 2229/20 (2013.01); B01J 2229/36 (2013.01); B01J 2229/37 (2013.01); B01J 2229/42 (2013.01); C07C 2529/40 (2013.01); Y02P 20/52 (2015.11)

(58) Field of Classification Search
CPC .. B01J 29/40; B01J 2229/186; B01J 2229/20; B01J 2229/42; B01J 2229/37; B01J 37/28; B01J 37/0209; B01J 37/0009; C07C 2529/40
USPC .......................................................... 502/71
See application file for complete search history.

(56) References Cited

U.S. PATENT DOCUMENTS

| 3,911,041 | A | | 10/1975 | Kaeding et al. | |
|---|---|---|---|---|---|
| 4,629,717 | A | | 12/1986 | Chao | |
| 4,900,704 | A | * | 2/1990 | McDaniel | C08F 10/00 502/208 |
| 5,190,902 | A | * | 3/1993 | Demmel | B01J 21/16 502/61 |
| 5,456,821 | A | * | 10/1995 | Absil | B01J 27/16 208/114 |
| 5,573,990 | A | | 11/1996 | Wang et al. | |
| 5,833,840 | A | * | 11/1998 | Absil | B01J 29/7007 208/113 |
| 6,645,461 | B1 | | 11/2003 | Unger et al. | |
| 6,797,851 | B2 | | 9/2004 | Martens et al. | |
| 7,229,941 | B2 | | 6/2007 | Burgfels et al. | |
| 7,230,151 | B2 | | 6/2007 | Martens et al. | |
| 7,368,410 | B2 | | 5/2008 | Ghosh et al. | |
| 9,174,204 | B2 | | 11/2015 | Burgfels et al. | |
| 9,511,361 | B2 | | 12/2016 | Burgfels et al. | |
| 2006/0173230 | A1 | * | 8/2006 | Chang | C07C 1/20 585/638 |

FOREIGN PATENT DOCUMENTS

| CN | 85102828 | | 7/1986 |
|---|---|---|---|
| CN | 101172916 | | 5/2008 |
| CN | 101172917 | | 5/2008 |
| CN | 101356138 | | 1/2009 |
| DE | 244030 | A3 | 3/1987 |
| DE | 3618964 | A1 | 12/1987 |
| DE | 272040 | A1 | 9/1989 |
| EP | 0448000 | A1 | 9/1991 |
| EP | 0 568 913 | * | 11/1993 |
| EP | 2025402 | A1 | 2/2009 |
| EP | 2348004 | A1 | 1/2010 |
| WO | 2007076088 | A2 | 7/2007 |
| WO | WO 2007/076088 | | 10/2007 |
| WO | 2009156434 | A2 | 12/2009 |
| WO | 2011044037 | A1 | 4/2011 |

OTHER PUBLICATIONS

International Search Report and Written Opinion, dated Jun. 12, 2012, with respect to International Application No. PCT/EP2012/054614.
International Search Report and Written Opinion, dated Jun. 12, 2012, with respect to International Application No. PCT/EP2012/054611.
English translation of German Patent and Trademark Office Examination Report, dated Oct. 21, 2011, with respect to German Patent Application 10 2011 013 909.5.
English machine translation for CN 85102828, Jul. 23, 1986.
Ehglish machine translation for CN 101172916, May 7, 2008.
English machine translation for CN 101172917, May 7, 2008.

* cited by examiner

Primary Examiner — Elizabeth D Wood
(74) Attorney, Agent, or Firm — Anthony A. Bisulca

(57) ABSTRACT

The present invention relates to a process for preparing a phosphorus containing zeolite type catalysts based on crystalline aluminosilicates, the catalysts of this process and the use of this catalysts for the conversion of methanol to olefins.

11 Claims, 2 Drawing Sheets

PROCESS FOR MANUFACTURE OF A ZEOLITE BASED CATALYST FOR THE CONVERSION OF METHANOL TO OLEFINS

The present invention relates to a process for preparing zeolite type catalyst based on crystalline aluminosilicates, the catalyst of this process and the use of this catalyst for the conversion of methanol to olefins.

BACKGROUND OF THE INVENTION

Zeolites have been widely studied for the conversion of methanol to hydrocarbons. Among them, ZSM-5 zeolite was the first zeolite studied as active catalyst for the conversion of oxygenates to hydrocarbons (D. Chang and A. J. Silvestri, Journal of Catalysis 47, 249-259 (1977)).

European patent application EP-A-0 448 000 relates to a process for the production of lower olefins from methanol by reacting a mixture containing methanol and/or dimethylether on crystalline aluminosilicates of the pentasil type having a Si/Al atomic ratio of at least 10. The only specifically disclosed catalyst is of the pentasil type and has a Si/Al atomic ratio of 103, a sodium content of about 340 ppm, a BET surface area of 342 m²/g and a pore volume of 0.33 cm³/g. This catalyst yields an olefin mixture of more than 6 wt.-% of ethylene, more than 40 wt.-% of propylene and less than 30 wt.-% of butenes from a methanol dimethylether mixture.

In the methanol to olefin conversion process deactivation of the catalyst by coke deposition has been a major drawback. The beneficial effect of decreasing the crystal size of the pentasil zeolites was shown EP-A-1 424 128 with higher selectivities to propylene and longer lifetime of the catalyst. Nonetheless the initial activity of the catalyst still is not fully recovered after regeneration when coke has been removed.

U.S. Pat. No. 3,911,041 discloses a catalyst comprising a crystalline aluminosilicate zeolite having a silica to alumina ratio of at least about 12 and a constraint index of about 1 to 12. The catalyst contains phosphorus incorporated with the crystal structure in an amount of about 3.5 to 4.8 wt.-%. The catalysts are used for the conversion of methanol and dimethylether to an olefin-containing reaction product. The methanol to olefin conversion is less than 2 wt.-%.

U.S. Pat. No. 5,573,990 discloses the conversion of methanol or dimethylether to light olefins by contacting methanol or dimethylether at a temperature of at least 400° C. with a zeolite ZSM-5 catalyst containing at least 0.7 wt.-% of phosphorus P and at least 0.97 wt.-% of rare earth element incorporated within the structure of the catalyst. The ZSM-5 based catalyst is prepared by: mixing a zeolite ZSM-5 catalyst with silica sol and an ammonium nitrate solution, kneading, moulding and calcining the mixture, ion exchanging with phosphoric acid under reduced pressure, drying and calcining the phosphorus modified zeolite, impregnating the phosphorus modified zeolite with a solution of rare earth elements under reduced pressure, drying and calcining the zeolite, and hydrothermally treating the obtained zeolite at 500-600° C. with water vapour.

U.S. Pat. No. 4,629,717 concerns a phosphorus modified alumina composite comprising a hydrogel having a molar ratio on an elemental basis of phosphorus to aluminum of 1:1 to 1:100 and a surface area of 140 to 450 m²/g. The composites are prepared by combining a phosphorus containing compound and an alumina hydrosol and gelling this mixture. This composite is used as a catalyst support in the hydrogenation of olefins.

U.S. Pat. No. 6,797,851 and U.S. Pat. No. 7,230,151 relate to a process of making olefins, particularly ethylene and propylene, from an oxygenate feed by use of two or more zeolite catalysts. The first catalyst may be a ZSM-5, the second catalyst contains a 10-ring molecular sieve, and is for example ZSM-22, ZSM-23, ZSM35 or ZSM-48. The amount of phosphorus, as measured on an elemental basis, is from 0.05 to 20 wt.-% based on the weight of the zeolite molecular sieve. The ZSM-5 catalyst may be unmodified, phosphorus modified or steam modified, however no specific catalysts or preparation methods thereof are disclosed.

U.S. Pat. No. 7,368,410 relates to a method for preparing zeolite catalysts comprising: treating a zeolite with a phosphorus compound to form a phosphorus-treated zeolite; heating the phosphorus-treated zeolite to a temperature of about 300° C. or higher; combining the phosphorus-treated zeolite with an inorganic oxide binder material to form a zeolite-binder mixture; and heating the zeolite-binder mixture at temperature of about 400° C. or higher to form a bound zeolite catalyst. The catalysts are used for the alkylation of aromatic compounds, especially for the methylation of toluene.

In EP-A-2 025 402 a phosphorus modified molecular sieve and its use in conversion of organics to olefins is disclosed. The molecular sieve may be prepared by: steaming a zeolite with a Si/Al ratio of below 30 at a temperature ranging from 550 to 680° C.; leaching with an aqueous phosphoric acid solution to remove a part of Al from the zeolite; separation of the zeolite from the liquid; optionally washing the zeolite; and calcining the zeolite.

The existing catalysts have the drawback of limited hydrothermal stability in the process for converting methanol into propylene. After extensive studies the present inventors were able to show that an improved catalyst for converting methanol to olefins can surprisingly be obtained by impregnating a previously conformed zeolite based catalyst with low amounts of phosphorus.

SUMMARY OF THE INVENTION

The present invention concerns a process for manufacturing a zeolite based catalyst comprising the following steps:
(a) adding an aluminum oxide and an acid to a zeolite powder of pentasil type, wherein the zeolite powder has an Si/Al atomic ratio of about 50 to about 250, and optionally kneading and homogenizing this mixture,
(b) forming, drying and calcining the mixture obtained in step (a) to obtain formed material,
(c) impregnating the formed material from step (b) with a phosphorus compound to obtain a phosphorus containing product, and
(d) calcining the phosphorus containing product from step (c) at a temperature in the range of from 150° C. to 800° C., to obtain a phosphorus containing catalyst.

This invention further relates to the catalysts which are obtained by the above process, wherein the amount of phosphorus in the catalyst is in the range of from 0.05 and 20 wt.-%, preferably in the range of from 0.5 and 10 wt.-%, more preferably in the range of from 1.0 to 4.0 wt.-%, most preferably in the range of from 1.5 to 2.5 wt.-%, on basis of the total weight of the catalyst.

This invention also relates to the use of these catalysts for converting methanol to olefins, especially for converting methanol to propylene.

DETAILED DESCRIPTION OF THE INVENTION

Figure 1:
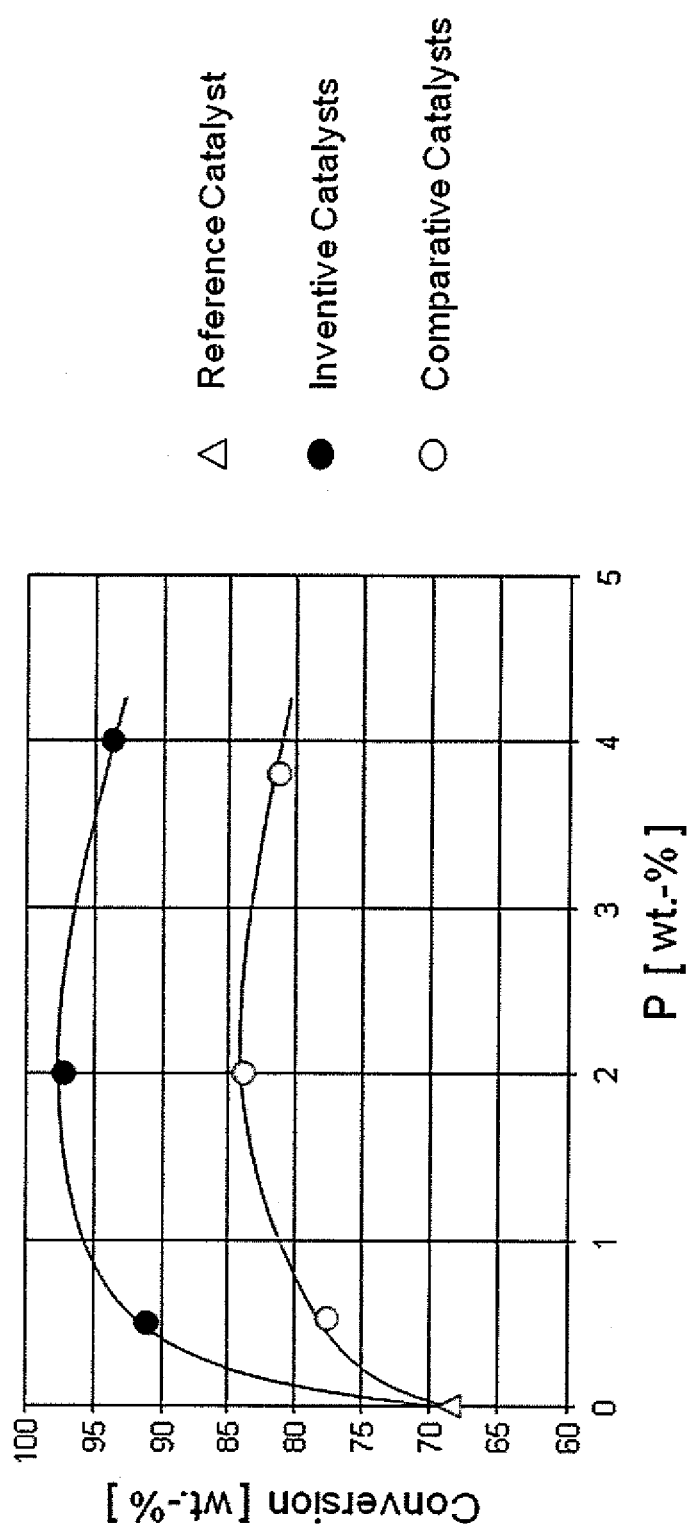
FIG. 1 shows the conversion rate of the reference (Δ), inventive (•) and comparative (○) catalysts after hydrothermal treatment in relation to the amount of phosphorus present in the catalysts.

The present invention relates to a preparation method of a catalyst, based on crystalline aluminosilicate, with high hydrothermal stability.

The inventive process for manufacturing a zeolite based catalyst comprises the following steps:
(a) adding an aluminum oxide and an acid to a zeolite powder of pentasil type, wherein the zeolite powder has an Si/Al atomic ratio of about 50 to about 250, and optionally kneading and homogenizing this mixture,
(b) forming, drying and calcining the mixture obtained in step (a) to obtain formed material,
(c) impregnating the formed material from step (b) with a phosphorus compound to obtain a phosphorus containing product, and
(d) calcining the phosphorus containing product from step (c) at a temperature in the range of from 150° C. to 800° C., preferably of from 200° C. to 600° C. to obtain a phosphorus containing catalyst.

The zeolite powder used in the inventive process has an Si/Al atomic ratio of about 50 to about 250, preferably of 50 to 250, more preferably of about 50 to about 150, even more preferably of 50 to 150, and most preferably of 75 to 120.

In this process the ratio of the phosphorus of the phosphorus compound to the zeolite powder preferably is in the range of 0.05 to 5.0 (wt./wt.), more preferably in the range of 0.1 to 2.0 (wt./wt.).

The phosphorus compound is preferably added in step (c) in such an amount that the phosphorus containing catalyst obtained in step (d) contains phosphorus in the range of from 0.05 to 20 wt.-%, preferably in the range of from 0.5 to 10 wt.-%, more preferably in the range of from 1.0 to 5.0 wt.-%, even more preferably in the range of from 1.0 to 4.0 wt.-%, most preferably in the range of from 1.5 to 2.5 wt.-%, on basis of the total weight of the catalyst.

The amount of aluminum oxide in the final catalyst is preferably 10 to 80 wt.-%, more preferably 10 and 40 wt.-% on basis of the total weight of the catalyst.

The phosphorus compound may be employed as a solid or in solution, preferably in an aqueous solution. It is preferred that the phosphorus compound is employed in solution. If the phosphorus compound is added to the formed material in step (c) in a solution, the obtained product is usually dried before being calcined in step (d). In another preferred embodiment the phosphorus containing product obtained in step (c) is not subjected to a washing step before being calcined in step (d).

When the phosphorus compound is employed in aqueous solution the temperature of the solution is chosen such as to favor the contact between the aluminum oxide and the phosphorus compound. When the phosphorus compound is employed without the addition of water or any other (organic or inorganic) solvent the mixture can be submitted to a milling step to favor the intimate contact between the phosphorus compound and catalyst composition. It is preferred that the phosphorus compound is employed in aqueous solution.

In the process of this invention, and in particular in step (b), drying is usually carried out for 5 min to 24 h, preferably for 1 h to 10 h. In the process of this invention, and in particular in step (b) and/or in step (d) (and especially in step (b) and in step (d)), calcining is usually carried out for 10 min to 10 h, preferably for 30 min to 6 h.

In the process of this invention, and in particular in step (b), drying is usually carried out at a temperature of from 20 to 150° C., more preferably of from 80 to 130° C., most preferably at about 100° C. In the process of this invention, and in particular in step (b), calcining is usually carried out at a temperature of from 160° C. to 800° C., preferably at a temperature of from 200° C. to 600° C.

In the inventive process, and in particular in step (b) and/or in step (d) (and especially in step (b) and in step (d)), calcination preferably is carried out without treatment with steam (water vapor). In particular, it is preferred that during calcination no steam is fed from the outside while heating the mixture. It is known in the art that steam treatment of zeolites results in dealumination of the zeolites and in an increase of the Si/Al atomic ratio. In the present invention, dealumination and transformation of the zeolite by steam is undesirable, and it is preferred that the zeolite framework is left untransformed and the Si/Al atomic ratio is left unchanged prior to preparing the formed material in step (b) and impregnating the formed material with a phosphorus compound.

Kneading as described in step (a) of this invention is usually carried out by using commercial available mixers, e.g. mixer with rotating mixing tool and fixed mixing chamber, mixer with rotating mixing tool and rotating mixing chamber.

Homogenizing as described in step (a) of this invention is usually carried out by using commercial available mixers, e.g. mixer with rotating mixing tool and fixed mixing chamber or mixer with rotating mixing tool and rotating mixing chamber. Prior to homogenizing, a lubricating agent such as, for example, steatite oil, may be added to the catalyst.

The forming process of step (b) may be any process known in the art for forming a catalytic mass into a desired shape. An exemplary forming process is extrusion of an extrudable mass with a commercial extruder such as, for example, a single-screw extruder or double-screw extruder, to extrudates. Said extrudates may optionally be granulated or pelletized. Other possible shapes are spherical or honeycomb structures. In a particularly preferred embodiment a plasticizable mass is formed into a desired shape, for example, by one of the above-mentioned processes, and is subsequently calcined for achieving the desired stability.

The order of addition of the individual components to obtain a plasticizable mass may be varied. For example, the aluminium oxide can be first blended with an aqueous acid and subsequently mixed with the zeolite powder. Alternatively, the solid compounds are mixed in a dry state and then combined with an aqueous acid.

In the process of the present invention the phosphorus compound is preferably selected from inorganic phosphorus containing acids, organic phosphorus containing acids, alkaline, earth alkaline and/or ammonium salts of inorganic phosphorus containing acids or organic phosphorus containing acids, phosphorus (V) halides, phosphorus (III) halides, phosphorus oxyhalides, phosphorus (V) oxide, phosphorus (III) oxide, and mixtures thereof.

It is further preferred in the process of the present invention that the phosphorus compound is selected from $PY_5$, $PY_3$, $POY_3$, $M_xE_{z/2}H_{3-(x+z)}PO_4$, $M_xE_{z/2}H_{3-(x+z)}PO_3$, $P_2O_5$, and $P_4O_6$, wherein:
Y represents F, Cl, Br or I, preferably Cl,
x=0, 1, 2, or 3,
z=0, 1, 2, or 3,
wherein x+z≤3,
M independently represents an alkaline metal and/or ammonium, and
E represents an earth alkaline metal.

It is even more preferred that the phosphorus compound employed in the process of the present invention is selected from $H_3PO_4$, $(NH_4)H_2PO_4$, $(NH_4)_2HPO_4$, and $(NH_4)_3PO_4$.

In the process of the present invention it is most preferred that the phosphorus compound is $(NH_4)H_2PO_4$.

In the process of the present invention the aluminum oxide used in step (a) is preferably aluminum oxide or aluminum oxide hydrate, most preferably aluminum oxide hydrate.

The acid used in step (a) of the process of the present invention is usually an inorganic or organic acid, preferably sulfuric acid, nitric acid, acetic acid, formic acid, oxalic acid or citric acid, more preferably nitric acid, acetic acid or citric acid, and most preferably nitric acid. It is further preferred that in step (b) the acid is applied in aqueous solution.

In a preferred embodiment the overall amount of phosphorus added in the inventive process is in the range of from 0.05 and 20 wt.-%, preferably in the range of from 0.5 and 10.0 wt.-%, more preferably in the range of from 0.5 and 4.0 wt.-%, most preferably in the range of from 1.5 to 2.5 wt.-% on basis of the total weight of the phosphorus modified catalyst.

In a further especially preferred embodiment the present invention provides a catalyst which can be obtained by the inventive process. The amount of phosphorus in this catalyst is usually in the range of from 0.05 and 20 wt.-%, preferably in the range of from 0.5 and 10.0 wt.-%, more preferably in the range of from 1.0 to 4.0 wt.-%, most preferably in the range of from 1.5 to 2.5 wt.-%, on basis of the total weight of the catalyst.

In a further preferred embodiment the catalyst of this invention has a Si/Al atomic ratio in the range from 50 to 150, preferably of from 75 to 120.

In another preferred embodiment, the catalyst of this invention has an Al:P atomic ratio of 2.5 or more, preferably in the range of 2.5 to 21.2, more preferably in the range of 4.0 to 15.0, and even more preferably in the range of 4.5 to 10.0. In further preferred embodiment, the catalyst of this invention has an Al:P atomic ratio in the range of 5.4 to 21.2. It is most preferably that the catalyst of this invention has an Al:P atomic ratio of about 5.4.

The zeolite employed in step (a) of the process of the present invention is a zeolite of the pentasil type. The zeolite can possess a structure as described in "Atlas of Zeolite Framework Types" (Ch. Baerlocher, W. M. Meier, D. H. Olson, Elsevier, Fifth Revised Edition, 2001), the disclosure of which in this connection is incorporated into this application by way of reference. Preferred zeolites of the present invention are zeolites having MFI or MEL structure. A preferred zeolite of the MFI structure is ZSM-5. A preferred zeolite of the MEL structure is ZSM-11. The zeolites employed in step (a) of the process of the present invention are preferably of the H-type, i.e., are protonated zeolites. Most preferably, the zeolite used in the present invention is H-type ZSM-5.

The zeolite employed in the process of the present invention has a pore size in the range of preferably 4.0 Å to 6.0 Å, more preferably in the range of 4.8 Å to 5.8 Å.

The zeolite powder of step (a) is preferably obtained by adding a template to the synthesis gel composition.

Preferred templates are tetraalkylammonium hydroxide such as tetrapropylammonium hydroxide (TPAOH), or tetrapropylammonium bromide (TPABr). Other templates that may be used in the preparation of the zeolite powder of step (a) are mixtures of ammonia or an organic amine compound with a further organic compound selected from the group of alcohols, preferably butyl alcohol.

The catalyst obtainable by the process of the present invention preferably has a pore volume, measured by means of mercury porosimetry according to DIN 66133, of 0.25 to 0.8 cm³/g, more preferably of 0.28 to 0.40 cm³/g The catalyst described in this invention is useful in a process for the conversion of methanol to olefins, especially propylene.

Hydrothermal stability of the catalysts can established by measuring the activity in the reaction of methanol to olefins, especially propylene, after calcination of the sample at temperatures from 700 to 750° C. in an atmosphere of 100% steam for a period of time of from 3 to 8 h. This treatment emulates in short time the long-term behavior of a methanol-to-propylene catalyst after many cycles of reaction-regeneration in which water is always present. It has been shown that the calcination in the presence of steam in the absence of phosphorus causes the dealumination of the zeolitic framework, resulting in the loss of the Brönsted acidity and consequently decreasing the activity and life time of the catalyst. With the addition of phosphorus distributed in both zeolite and alumina binder, as claimed in the present invention, the activity of the catalyst is preserved.

EXAMPLES

Reference Example 1

61 kg of deionized water and 57 kg of a commercially available, peptizable aluminum oxide hydrate (Pural SB®, Sasol) having a particle size distribution of 91% by volume≤90 µm; 51% by volume≤45 µm, and 27% by volume≤25 µm were blended in a commercial kneader. A solution of 39 kg 57.2% nitric acid and 30 kg deionized water were slowly added. The resulting solution was kneaded for 60 minutes until plasticization and homogenization had occurred. Subsequently 235 kg of calcined H-zeolite powder with a silicon-to-aluminum atomic ratio of 105 and an average particle diameter of the primary crystals of 0.03 µm, which had been ground to a particle size of less than about 500 µm by means of a commercial mill, were added. Mixing was continued for another 30 minutes, and about 25 kg of additional water was added to improve the consistency of the compound. After blending in 20 kg of steatite oil and mixing for another 10 minutes, the plasticized compound was extruded in a commercial extruder into shaped articles having a diameter of about 3 mm and a length of about 5 mm. The shaped articles were then dried for 16 hours at 120° C. and subsequently calcined for 5 hours at 600° C.

This catalyst is hereinafter identified as Reference Example 1. The chemical composition of the catalyst is shown in Table 1.

Example 1

A 100 ml spherical flask is charged with 10 ml redistilled water and 0.019 g ammonium dihydrogen phosphate (99 wt.-%) under stirring. To the obtained solution, 1 g of the catalysts of Reference Example 1, previously ground to a granulate with a particle size of 0.2 to 0.4 mm, are added. This suspension is slowly evaporated (1 hour) in a rotary vacuum evaporator at 80° C. until dryness. The solid product is further dried at 100° C. for 2 h and calcined at 650° C. for 3 h. The obtained catalyst has a P content of 0.5 wt.-% on basis of the total weight of the catalyst. The chemical composition of the catalyst is shown in Table 1.

Examples 2 to 3

The catalysts of examples 2 to 3 were obtained analogously to example 1 by using 0.075 g and 0.15 g ammonium dihydrogen phosphate, respectively. They have a P content of 2.0 wt.-%, and 4.0 wt.-%, respectively, on basis of the total weight of the catalyst. The chemical compositions of these catalysts are shown in Table 1.

TABLE 1

Chemical composition and Al:P ratio of the catalysts of Ref.-Example 1 and Examples 1 to 3

| Catalyst | Ref.-Example 1 | Example 1 | Example 2 | Example 3 |
|---|---|---|---|---|
| P wt.-% | 0 | 0.5 | 2.0 | 4.0 |
| $SiO_2$ wt.-% | 82.6 | 81.7 | 79.1 | 75.2 |
| $Al_2O_3$ wt.-% | 17.4 | 17.2 | 16.7 | 15.8 |
| $P_2O_5$ wt.-% | 0 | 1.1 | 4.3 | 8.9 |
| Al:P (mol/mol) | — | 21.2 | 5.4 | 2.5 |

Comparative Example 1

175 g demineralized water and 175 g commercially available, peptizable aluminum oxide hydrate (Pural SB®, Sasol) with a particle size distribution from 91 Vol.-%≤90 µm; 51 Vol.-%≤45 µm and 27 Vol.-%≤25 µm were mixed in a commercially available double-Z-Kneader. 214 g of a 30 wt.-% nitric acid solution were slowly added and this mixture homogenized until plastification occurred.

Then 16 g orthophosphoric acid (85 wt.-%) and subsequently 700 g calcined H-zeolite powder with a silicon-to-aluminum atomic ratio of 105 and an average particle diameter of the primary crystals of 0.03 µm, which had been ground to a particle size of less than 500 µm by means of a commercial mill, were slowly added to the mixture under kneading. After addition of 10 g steatite oil and approximately 14 g demineralized water the mixture was homogenized. The homogenized mixture was then blown with air until an extrudable mass was obtained. The mass was extruded with a commercially available single-screw extruder to extrudates with a diameter of approximately 3 mm and a length of approximately 6 mm. These extrudates were dried at 120° C. for 16 h and then calcined at 550° C. for 5 h.

The obtained extrudate is hereinafter identified as Comparative Example 1 and has a P content of 0.5 wt.-% on basis of the total weight of the catalyst. The chemical composition is shown in Table 2.

Comparative Examples 2 to 4

The catalysts of comparative examples 2, 3 and 4 were obtained analogously to comparative example 1 by using 64 g, 127 g respectively 190 g orthophosphoric acid (85 wt.-%). The obtained catalysts have a P content of 2.0, 3.8 and 5.5 wt.-% on basis of the total weight of the catalyst. The chemical compositions of these catalysts are shown in Table 2.

TABLE 2

Chemical composition and Al:P ratio of the catalysts of Comparative Examples 1 to 4.

| Catalyst | Comp.-Example 1 | Comp.-Example 2 | Comp.-Example 3 | Comp.-Example 4 |
|---|---|---|---|---|
| P wt.-% | 0.5 | 2.0 | 3.8 | 5.5 |
| $SiO_2$ wt.-% | 82.8 | 79.7 | 76.1 | 72.7 |
| $Al_2O_3$ wt.-% | 16.1 | 15.6 | 14.9 | 14.3 |
| $P_2O_5$ wt.-% | 1.1 | 4.7 | 9.0 | 13 |
| Al:P (mol/mol) | 20.0 | 4.6 | 2.3 | 1.5 |

Application Examples

The hydrothermal stability of the catalysts was measured by performing the reaction of methanol to propylene in the presence of the catalysts which had previously been subjected to a hydrothermal treatment. The hydrothermal treatment was carried out as follows: The catalysts were pelletized to a particle size in the range of 0.2 to 0.4 mm and placed in small crucibles in an oven. Then they were subjected to a temperature of about 700° C. for about 5 h, with continuous feeding of water at 1.5 ml/min.

The hydrothermally treated samples were tested in an isothermal fixed bed reactor for the conversion of methanol to propylene. The reaction conditions used were:

methanol/water=1:2 wt./wt.

weight hourly space velocity

WHSV(MeOH)=1 $h^{-1}$, WHSV($H_2O$)=2 $h^{-1}$ outlet pressure=1.02 bar reaction temperature=450° C.

amount of catalyst=0.5 g particle size: 0.2 to 0.4 mm.

The methanol-water mixture was fed by means of a KDS dual syringe pump. 0.5 g catalyst was placed in a glass reactor of 15 mm diameter and the temperature was controlled by means of a k-thermocouple inserted inside the bed. Above the catalyst bed a bed of quartz sand was placed to ensure a good vaporization of the feed.

The outlet of the reactor was thermostatized at 150° C. and the products were automatically analyzed each 30 min in two Gas Chromatographs HP5890 with FID detectors. First, with a capillary column HP-PONA 50 m 0.25 mm ID, that allows the separation of methane, ethane ethylene, propane+propylene, dimethylether, methanol+isobutane, n-butane, butenes, and C5+ (higher hydrocarbons), with a temperature program starting at 30° C. up to 250° C. Second, in a Plot-Alumina column with dimensions of 30 m and 0.53 mm, for the separation of ethane, ethylene, propane, propylene and isobutane, with a temperature program from 50° C. to 190° C.

Conversion is defined as the sum of the yields of products different from methanol and dimethylether relative to the sum of the yields of all products of educts.

The kinetic rate of a catalyst is an indication of its activity. It may be described by its second order kinetic rate constant which can be used for comparison of catalysts tested at the same spatial velocity. The rate constant may be calculated as follows:

$$\text{rate constant} = \frac{\text{conversion}}{100 \text{ wt. \%} - \text{conversion}}.$$

Figure 2:
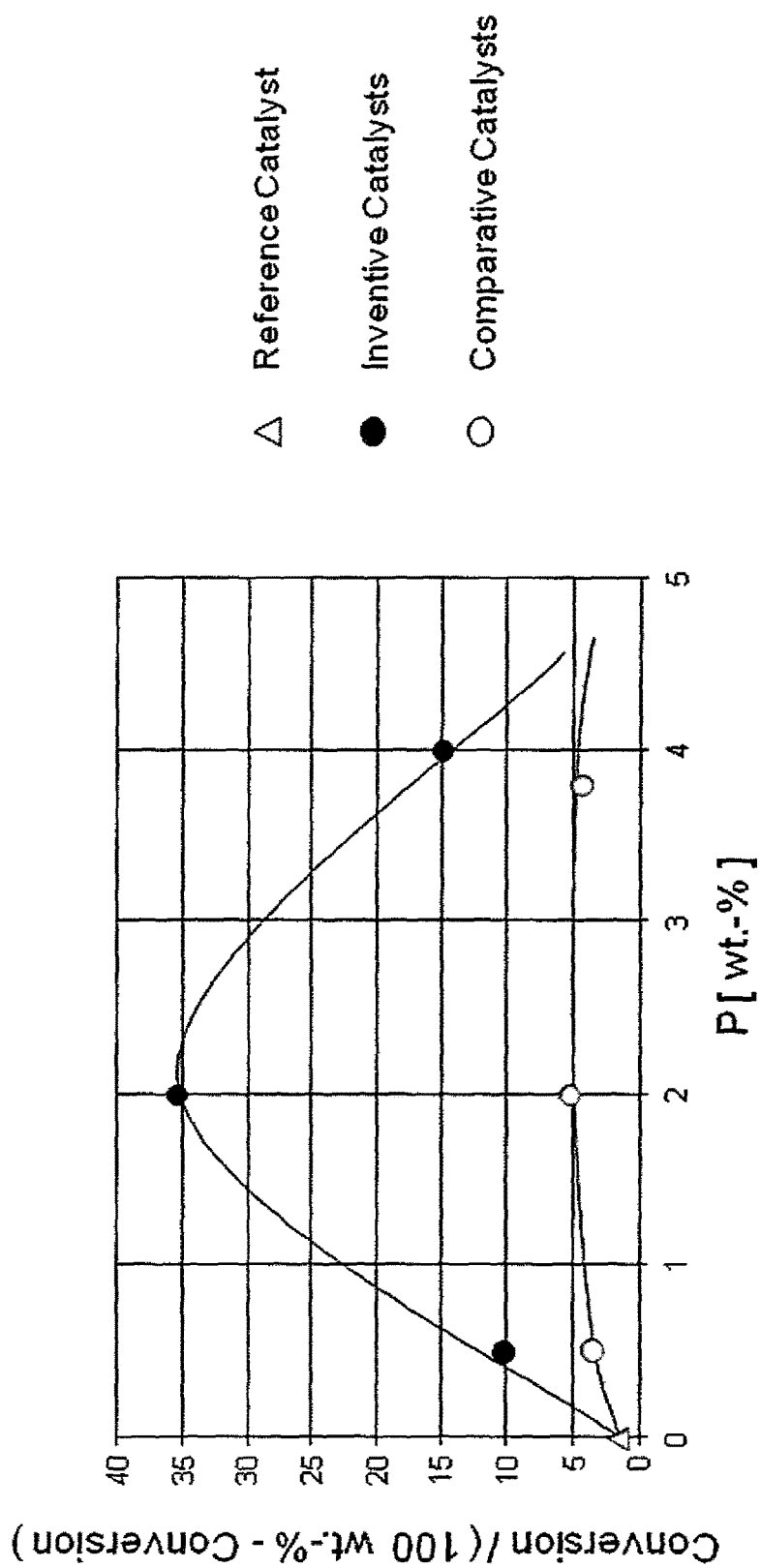
FIG. 2 shows the second order kinetic rate constant of the reference (Δ), inventive (•) and comparative (○) catalysts after hydrothermal treatment in relation to the amount of phosphorus present in the catalysts.

The catalysts from Reference Example 1, Examples 1 to 3 and Comparative Examples 1 to 4 were tested after hydrothermal treatment at 700° C. for 5 h in the reaction of methanol to propylene. The conversion percentage, kinetic rate constants and the yields of the products different from methanol and dimethylether are shown in Table 3. The conversion and the kinetic rate are additionally displayed in FIGS. 1 and 2.

TABLE 3

Conversion, kinetic rate and yields of catalysts of reference example 1, inventive examples
1 to 3 and comparative examples 1 to 4 after hydrothermal treatment at 700° C. for 5 hours.

| Catalyst | Conversion [wt.-%] | Kinetic rate constant | Yield [wt.-%] | | | | | | |
|---|---|---|---|---|---|---|---|---|---|
| | | | H2 + C1 | Ethylene | Ethane | Propylene | Propane | Total C4 | Total C5+ |
| Ref.-Ex. 1 | 68.7 | 2.2 | 0.6 | 2.3 | 0.03 | 22.0 | 0.6 | 15.5 | 27.6 |
| Ex. 1 | 91.0 | 10.1 | 1.0 | 6.3 | 0.09 | 27.0 | 2.0 | 19.9 | 34.7 |
| Ex. 2 | 97.3 | 36.0 | 0.8 | 9.3 | 0.10 | 30.2 | 2.8 | 20.5 | 33.6 |
| Ex. 3 | 93.7 | 14.9 | 0.7 | 7.4 | 0.09 | 32.2 | 2.0 | 21.5 | 29.9 |
| Comp.-Ex. 1 | 77.5 | 3.4 | 0.9 | 4.3 | 0.11 | 24.8 | 1.4 | 16.7 | 29.3 |
| Comp.-Ex. 2 | 83.9 | 5.2 | 2.4 | 7.9 | 0.18 | 25.4 | 1.8 | 17.3 | 28.9 |
| Comp.-Ex. 3 | 81.3 | 4.3 | 1.5 | 6.4 | 0.13 | 25.0 | 1.5 | 16.5 | 30.2 |
| Comp.-Ex. 4 | 79.7 | 3.9 | 1.7 | 8.1 | 0.16 | 25.3 | 1.8 | 16.5 | 26.1 |

It can be clearly seen that the catalysts of inventive examples 1 to 3 which have been impregnated with a phosphorus compound after combining the zeolite powder with the aluminum oxide yield higher conversions than the comparative catalysts where the phosphorus is bound within the zeolite matrix. Moreover, when activity is measured in terms of second order kinetic rate constant, the activity of the inventive catalysts is up to six times higher than of the comparative catalysts. In addition, the yield of propylene substantially increases for the inventive catalysts.

The invention claimed is:

1. A process for manufacturing of a zeolite based catalyst comprising the following steps:
   (a) adding an aluminum oxide and an acid to a zeolite powder of pentasil type, wherein the zeolite powder has an Si/Al atomic ratio of about 50 to about 250 and is of the H form,
   (b) forming, drying and calcining, without treatment with steam, the mixture obtained in step (a) to obtain formed material,
   (c) impregnating the formed material of step (b) with a phosphorus compound to obtain a phosphorus containing product, and
   (d) calcining the phosphorus containing product from step (c) at a temperature in the range of from 150° C. to 800° C., to obtain a phosphorus containing catalyst
   wherein the amounts of the aluminum oxide added in step (a), and of the phosphorus compound added in step (c) are chosen such that the Al:P atomic ratio in the phosphorus containing catalyst obtained in step (d) is 2.5 or more.

2. The process according to claim 1, wherein the zeolite powder has an Si/Al atomic ratio of about 50 to about 150.

3. The process according to claim 1, wherein the phosphorus compound is added to step (c) in such an amount that the amount of phosphorus in the phosphorus containing catalyst obtained in step (d) is in the range of from 0.05 to 20 wt.-%, on basis of the total weight of the catalyst.

4. The process according to claim 1, wherein the phosphorus compound is selected from the group consisting of inorganic phosphorus containing acids, organic phosphorus containing acids, alkaline, earth alkaline and ammonium salts of inorganic phosphorus containing acids and organic phosphorus containing acids, phosphorus (V) halides, phosphorus (III) halides, phosphorus oxyhalides, phosphorus (V) oxide, phosphorus (Ill) oxide, and mixtures thereof.

5. The process according to claim 1, wherein the phosphorus compound is selected from the group consisting of $PY_5$, $PY_3$, $POY_3$, $M_xE_{z/2}H_{3-(x+z)}PO_4$, $M_xE_{z/2}H_{3-(x+z)}PO_3$, $P_2O_5$, and $P_4O_6$, wherein:
   Y represents F, Cl, Br or I,
   x=0, 1, 2, or 3,
   z=0, 1, 2, or 3,
   wherein x+z≤3,
   M represents an alkaline metal and/or ammonium, and
   E represents an earth alkaline metal.

6. The process according to claim 1, wherein the phosphorus compound is selected from the group consisting of $H_3PO_4$, $(NH_4)H_2PO_4$, $(NH_4)_2HPO_4$, and $(NH_4)_3PO_4$.

7. The process according to claim 6, wherein the phosphorus compound comprises $(NH_4)H_2PO_4$.

8. The process according to claim 1, wherein the aluminum oxide used in step (a) comprises aluminum oxide hydrate.

9. The process according to claim 1, wherein the acid used in step (a) is selected from the group consisting of sulfuric acid, nitric acid, acetic acid and citric acid.

10. The process of claim 1, wherein the zeolite powder has an Si/Al atomic ratio of 75 to 120.

11. The process of claim 1, wherein the Al:P atomic ratio is in the range of 2.5 to 21.2.

* * * * *